United States Patent
Chen et al.

(10) Patent No.: US 9,963,406 B2
(45) Date of Patent: May 8, 2018

(54) HYDROCARBON CONVERSION

(71) Applicant: ExxonMobil Chemical Patents Inc., Baytown, TX (US)

(72) Inventors: Tan-Jen Chen, Kingwood, TX (US); Paul F. Keusenkothen, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days. days.

(21) Appl. No.: 15/240,666

(22) Filed: Aug. 18, 2016

(65) Prior Publication Data
US 2017/0088490 A1 Mar. 30, 2017

Related U.S. Application Data

(60) Provisional application No. 62/232,609, filed on Sep. 25, 2015, provisional application No. 62/234,240, filed on Sep. 29, 2015.

(30) Foreign Application Priority Data

Nov. 19, 2015 (EP) ..................... 15195311
Dec. 3, 2015 (EP) ..................... 15197698

(51) Int. Cl.
*C07C 2/12* (2006.01)
*C07C 2/76* (2006.01)
(Continued)

(52) U.S. Cl.
CPC ............ *C07C 5/3335* (2013.01); *B01J 21/04* (2013.01); *B01J 21/08* (2013.01); *B01J 21/12* (2013.01);
(Continued)

(58) Field of Classification Search
None
See application file for complete search history.

(56) References Cited

U.S. PATENT DOCUMENTS 3,702,886 A 11/1972 Argauer et al.
3,760,024 A 9/1973 Cattanach
(Continued)

FOREIGN PATENT DOCUMENTS

| | | |
|---|---|---|
| EP | 0293032 | 11/1988 |
| WO | 1997/017290 | 5/1997 |
| WO | 2010/140005 | 12/2010 |

OTHER PUBLICATIONS

Tabak, S. A., A. A. Avidan, and F. J. Krambeck. "Production of Synthetic Gasoline and Diesel Fuel from Non-Petroleum Resources." *Prepr Pap-Am Chem Soc Div Fuel Chem* 31 (1986): 293-299.

*Primary Examiner* — Tam M Nguyen

(57) ABSTRACT

The invention relates to the conversion of paraffinic hydrocarbon to oligomers of greater molecular weight and/or to aromatic hydrocarbon. The invention also relates to equipment and materials useful in such conversion, and to the use of such conversion for, e.g., natural gas upgrading. Corresponding olefinic hydrocarbon is produced from the paraffinic hydrocarbon in the presence of a dehydrogenation catalyst containing a catalytically active carbonaceous component. The corresponding olefinic hydrocarbon is then converted by oligomerization and/or dehydrocyclization in the presence of at least one molecular sieve catalyst.

11 Claims, 1 Drawing Sheet

(51) Int. Cl.

| | |
|---|---|
| C07C 5/333 | (2006.01) |
| B01J 21/12 | (2006.01) |
| B01J 21/08 | (2006.01) |
| B01J 21/04 | (2006.01) |
| B01J 21/18 | (2006.01) |
| B01J 23/42 | (2006.01) |
| B01J 23/44 | (2006.01) |
| B01J 23/46 | (2006.01) |
| B01J 23/22 | (2006.01) |
| B01J 23/26 | (2006.01) |
| B01J 23/34 | (2006.01) |
| B01J 23/745 | (2006.01) |
| B01J 23/75 | (2006.01) |
| B01J 23/755 | (2006.01) |
| B01J 23/28 | (2006.01) |
| B01J 23/52 | (2006.01) |
| B01J 27/055 | (2006.01) |
| B01J 27/053 | (2006.01) |
| B01J 27/04 | (2006.01) |
| B01J 27/043 | (2006.01) |
| B01J 27/045 | (2006.01) |
| B01J 27/051 | (2006.01) |
| B01J 27/047 | (2006.01) |
| B01J 27/232 | (2006.01) |
| B01J 27/25 | (2006.01) |
| B01J 35/10 | (2006.01) |

(52) U.S. Cl.
CPC ............ *B01J 21/18* (2013.01); *B01J 21/185* (2013.01); *B01J 23/22* (2013.01); *B01J 23/26* (2013.01); *B01J 23/28* (2013.01); *B01J 23/34* (2013.01); *B01J 23/42* (2013.01); *B01J 23/44* (2013.01); *B01J 23/462* (2013.01); *B01J 23/464* (2013.01); *B01J 23/52* (2013.01); *B01J 23/745* (2013.01); *B01J 23/75* (2013.01); *B01J 23/755* (2013.01); *B01J 27/04* (2013.01); *B01J 27/043* (2013.01); *B01J 27/045* (2013.01); *B01J 27/047* (2013.01); *B01J 27/051* (2013.01); *B01J 27/053* (2013.01); *B01J 27/055* (2013.01); *B01J 27/232* (2013.01); *B01J 27/25* (2013.01); *B01J 35/1014* (2013.01); *B01J 35/1038* (2013.01); *C07C 2/12* (2013.01); *C07C 2/76* (2013.01); *C07C 2529/06* (2013.01)

(56) References Cited

U.S. PATENT DOCUMENTS

| | | |
|---|---|---|
| 3,832,449 A | 8/1974 | Rosinski et al. |
| 3,960,978 A | 6/1976 | Givens et al. |
| 4,016,245 A | 4/1977 | Plank et al. |
| 4,021,501 A | 5/1977 | Dyer et al. |
| 4,021,502 A | 5/1977 | Plank et al. |
| 4,076,842 A | 2/1978 | Plank et al. |
| RE29,948 E | 3/1979 | Dwyer et al. |
| 4,150,062 A | 4/1979 | Garwood et al. |
| 4,211,640 A | 7/1980 | Garwood et al. |
| 4,227,992 A | 10/1980 | Garwood et al. |
| 4,268,707 A * | 5/1981 | Antos ................. B01J 23/8946 585/434 |
| 4,439,409 A | 3/1984 | Puppe et al. |
| 4,456,781 A | 6/1984 | Marsh et al. |
| 4,556,477 A | 12/1985 | Dwyer |
| 4,855,522 A | 8/1989 | Diaz |
| 4,954,325 A | 9/1990 | Rubin et al. |
| 5,026,937 A | 6/1991 | Bricker |
| 5,236,575 A | 8/1993 | Bennett et al. |
| 5,250,277 A | 10/1993 | Kresge et al. |
| 5,362,697 A | 11/1994 | Fung et al. |
| 5,633,417 A | 5/1997 | Beck et al. |
| 5,675,047 A | 10/1997 | Beck et al. |
| 5,936,135 A | 8/1999 | Choudhary et al. |
| 6,077,498 A | 6/2000 | Diaz Cabanas et al. |
| 6,670,517 B1 | 12/2003 | Abichandani et al. |
| 7,186,871 B2 | 3/2007 | Mitchell et al. |
| 8,692,043 B2 | 4/2014 | Lauritzen et al. |
| 8,835,706 B2 | 9/2014 | Iyer et al. |
| 9,790,435 B2 * | 10/2017 | Sari .......................... C10G 3/47 |
| 2009/0030253 A1 | 1/2009 | Xu et al. |
| 2009/0209794 A1 | 8/2009 | Lauritzen et al. |
| 2014/0256536 A1 | 9/2014 | Lauritzen et al. |

\* cited by examiner

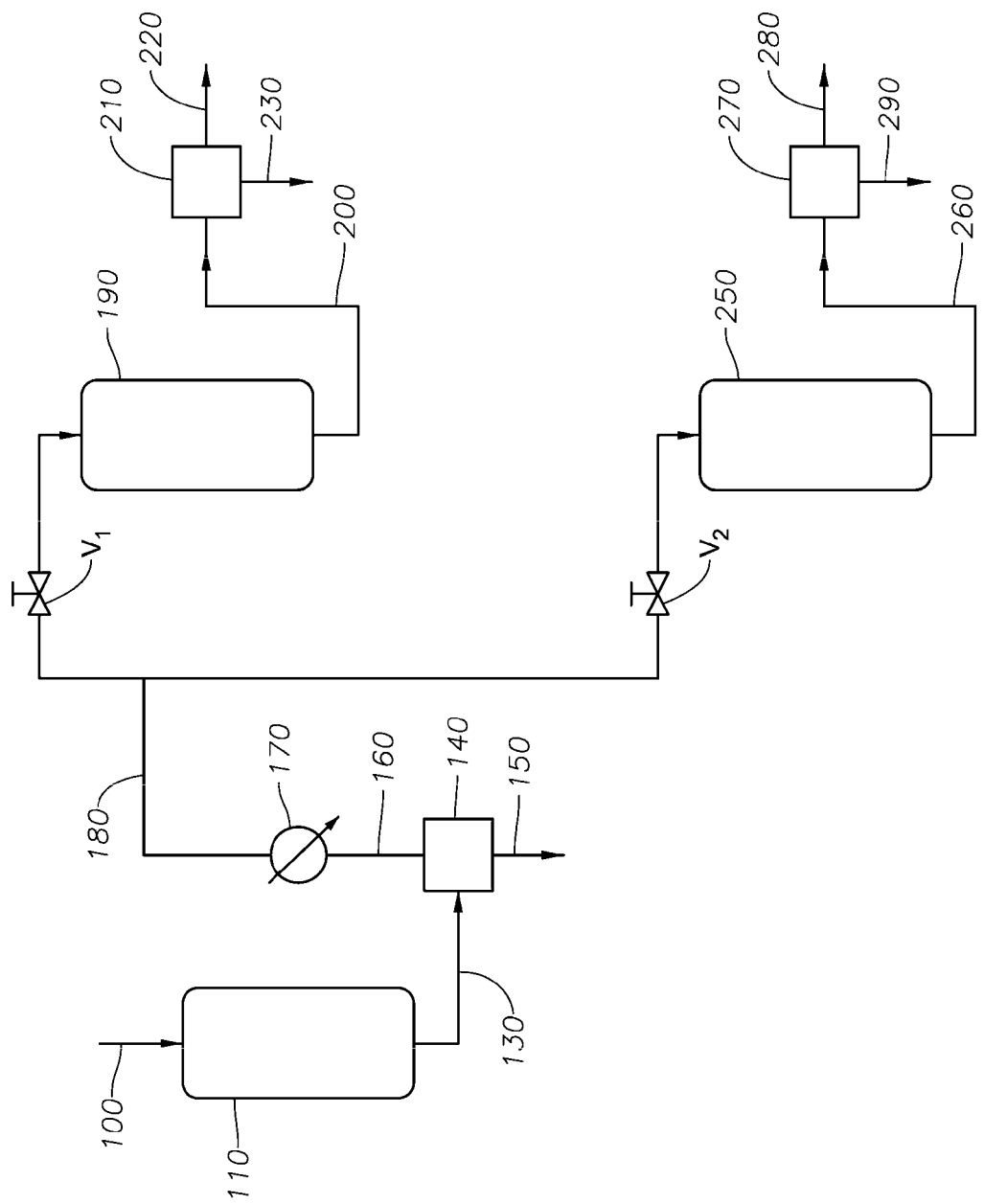

HYDROCARBON CONVERSION

CROSS-REFERENCE TO RELATED APPLICATIONS

This application claims priority to and the benefit of U.S. Patent Application Nos. 62/232,609 filed Sep. 25, 2015 and 62/234,240, filed Sep. 29, 2015; and European Application Nos. 15195311.4 filed Nov. 19, 2015 and 15197698.2, filed Dec. 3, 2015, all of which are incorporated by reference in their entireties. The following related cases are also incorporated by reference in their entireties: U.S. Patent Application No. 62/234,262; European Application No. 15195314.8; U.S. Patent Application No. 62/247,795; European Application No. 15197700.6; U.S. Patent Application No. 62/248,374; European Application No. 15197702.2; U.S. Patent Application No. 62/253,268; U.S. Patent Application No. 62/298,655; European Application No. 16167672.1; U.S. Patent Application No. 62/326,918; European Application No. 16175163.1; U.S. Patent Application No. 62/299,730; European Application No. 16167395.9; U.S. Patent Application No. 62/313,288; European Application No. 16173587.3; U.S. Patent Application No. 62/313,306 and European Application No. 16173980.0.

FIELD OF INVENTION

The invention relates to the conversion of paraffinic hydrocarbon to oligomer of greater molecular weight and/or to aromatic hydrocarbon. The invention also relates to equipment and materials useful in such conversion, and to the use of such conversion for, e.g., natural gas upgrading.

BACKGROUND $C_{5+}$ hydrocarbon, such as aromatic hydrocarbon and/or $C_{5+}$ oligomer of light hydrocarbon, is frequently used as blending components for transportation fuels. In addition to this use, aromatic hydrocarbon is also used for producing petrochemicals such as styrene, phenol, nylon and polyurethanes and many others. $C_{5+}$ hydrocarbon can be produced by cracking a light hydrocarbon stream such as ethane in the presence of steam (steam cracking). Exposing the combined ethane-steam feed to steam cracking conditions produces a product comprising molecular hydrogen, $C_{4-}$ olefin, other $C_{4-}$ hydrocarbon, and $C_{5+}$ hydrocarbon, such as $C_{5+}$ oligomer. The yield of aromatic hydrocarbon and $C_{5+}$ oligomer from steam cracking is generally much less than the yield of light hydrocarbon. Consequently, complex processes typically are needed for separating and recovering aromatic hydrocarbon and $C_{5+}$ oligomer from steam cracker effluent. Catalytic naphtha reforming produces a product having a much greater content of aromatic hydrocarbon than steam cracker effluent, but the naphtha feed is itself useful for other purposes such as a motor gasoline blendstock.

Various attempts have been made to overcome these difficulties, and provide an efficient process for producing $C_{5+}$ hydrocarbon at high yield from a relatively inexpensive feed. For example, processes have been developed for producing light aromatic hydrocarbon (e.g., benzene, toluene, and xylenes-"BTX") from paraffinic $C_{4-}$ feeds. The processes typically utilize an acidic molecular sieve such as ZSM-5 and at least one metal having dehydrogenation functionality, such as one or more of Pt, Ga, Zn, and Mo. These conventional processes typically operate at high temperature and low pressure. Although these conditions are desirable for producing aromatic hydrocarbon, they also lead to undue catalyst deactivation as a result of increased catalyst coking. Catalyst coking generally worsens under conditions which increase feed conversion, leading to additional operating difficulties.

One way to lessen the amount of catalyst coking is disclosed in U.S. Pat. No. 5,026,937. The reference discloses removing $C_{2+}$ hydrocarbon from the feed in order to increase the feed's methane concentration. Since ethane, propane, and butanes are less refractory, removing these compounds from the feed decreases the amount of over-cracking, and lessens the accumulation of catalyst coke. The process utilizes a catalyst comprising molecular sieve, an amorphous phosphorous-modified alumina, and at least one dehydrogenation metal selected from Ga, Pt, Rh, Ru, and Ir. The catalyst contains ≤0.1 w t. % of Ni, Fe, Co, Group VIb metals, and Group VIIb metals. The reference also discloses increasing aromatic hydrocarbon yield by removing hydrogen from the reaction, e.g., by combusting the hydrogen with oxygen in the presence of an oxidation catalyst that has greater selectivity for hydrogen combustion over methane combustion.

Processes have also been developed for converting less-refractory paraffinic hydrocarbon to aromatic hydrocarbon with decreased selectivity for catalyst coke. For example, U.S. Pat. No. 4,855,522 discloses converting $C_2$, $C_3$, and $C_4$ paraffinic hydrocarbon with increased selectivity for aromatic hydrocarbon and decreased selectivity for catalyst coke. The process utilizes a dehydrocyclization catalyst comprising (a) an aluminosilicate having a silica:alumina molar ratio of at least 5 and (b) a dehydrogenation compound of (i) Ga and (ii) at least one rare earth metal. The reference discloses carrying out the aromatization conversion at a space velocity (LHSV) in the range of from 0.5 to 8 $hr^{-1}$, a temperature ≥450° C. (e.g., 475° C. to 650° C.), a pressure of from 1 bar to 20 bar, and a feed contact time of 1 to 50 seconds.

More recently, U.S. Pat. No. 7,186,871 discloses that increasing the catalyst's dehydrogenation metal loading lessens the amount of catalyst coking. Although coking is lessened, increasing dehydrogenation metal loading has been found to increase the catalyst's hydrogenolysis activity, resulting in an increase in the amount of methane and other light saturated hydrocarbon in the reaction product and a decrease in the amount of the desired aromatic hydrocarbon.

There is a need, therefore, for processes which selectively convert light paraffinic hydrocarbon to $C_{5+}$ hydrocarbon at high conversion with decreased yield of catalyst coke and a decreased yield of hydrogenolysis byproducts compared to conventional processes.

SUMMARY

In certain aspects, the invention relates to a process for producing aromatics. The process includes reacting a feed in the presence of the first catalyst under catalytic dehydrogenation conditions. The feed comprises ≥1 wt. % of a first hydrocarbon and further comprises a second hydrocarbon, wherein the (i) the first hydrocarbon comprises $C_{n+}$ paraffinic hydrocarbon, (ii) the second hydrocarbon comprises $C_{m-}$ hydrocarbon, (iii) n is a positive integer ≥2 and m is a positive integer ≤n−1, (iv) the feed has a first hydrocarbon: second hydrocarbon molar ratio in the range of from 0.001 to 100. The dehydrogenation conditions are effective for dehydrogenating ≥10 wt. % of the of the $C_{n+}$ paraffinic hydrocarbon of the feed's first hydrocarbon, to produce a first product comprising corresponding olefinic hydrocarbon, $C_{m-}$ hydrocarbon, and molecular hydrogen. The first multi-component catalyst has dehydrogenation functionality and comprises (i) ≥10 wt. % of at least one inorganic oxide component having a surface area ≥10 m²/g and a pore volume ≥0.1 ml/g, (ii) ≥0.01 wt. % of at least one catalytically active carbonaceous component, and (iii) ≥0.05 wt. % of at least one element selected from Groups 5-11 of the Periodic Table. The process further comprises reacting ≥10 wt. % of the first product's corresponding olefinic hydrocarbon in the presence of a second catalyst under catalytic dehydrocyclization conditions to produce a second product comprising aromatics and additional molecular hydrogen. The second multi-component catalyst has dehydrocyclization functionality and comprises ≥10 wt. % of a molecular sieve component and ≥0.005 wt. % of a dehydrogenation component comprising at least one element selected from Groups 3 to 13 of the Periodic Table.

In other aspects, the invention relates to a process for producing $C_{5+}$ oligomers. The process includes reacting a feed in the presence of a first catalyst under catalytic dehydrogenation conditions. The feed comprises ≥1 wt. % of a first hydrocarbon and further comprises a second hydrocarbon, wherein the (i) the first hydrocarbon comprises $C_{n+}$ paraffinic hydrocarbon, (ii) the second hydrocarbon comprises $C_{m-}$ hydrocarbon, (iii) n is a positive integer ≥2 and m is a positive integer ≤n−1, and (iv) the feed has a first hydrocarbon:second hydrocarbon molar ratio in the range of from 0.001 to 100. The first catalyst has dehydrogenation functionality and comprises (i) ≥10 wt. % of at least one inorganic oxide component having a surface area ≥10 m²/g and a pore volume ≥0.1 ml/g, (ii) ≥0.01 wt. % of at least one catalytically active carbonaceous component, and (iii) ≥0.05 wt. % of at least one element selected from Groups 5-11 of the Periodic Table. The reaction is carried out under conditions effective for dehydrogenating ≥10 wt. % of the of the $C_{n+}$ paraffinic hydrocarbon of the feed's first hydrocarbon, to produce a first product comprising corresponding olefinic hydrocarbon, $C_{m-}$ hydrocarbon, and molecular hydrogen. The process further comprises reacting ≥10 wt. % of the first product's corresponding olefinic hydrocarbon in the presence of a second catalyst under catalytic oligomerization conditions including a temperature in the range of from 260° C. to 500° C., a hydrocarbon partial pressure in the range of 50 kPa to 4000 kPa, and a space velocity (WHSV) ≥0.1 hr⁻¹, to produce a product comprising $C_{5+}$ oligomer derived from the reacted corresponding olefinic hydrocarbon. The second catalyst has oligomerization functionality and comprises ≥10 wt. % of at least one molecular sieve having a Constraint Index in the range of from 1 to 12 and an α≤250.

Other aspects of the invention relate to a process for producing aromatic hydrocarbon. The process includes producing a first catalyst by contacting a catalyst precursor with a synthesis hydrocarbon. The catalyst precursor comprises at least one element selected from Groups 5-11 of the Periodic Table and at least one inorganic oxide having a surface area ≥10 m²/g and a pore volume ≥0.1 ml/g. The synthesis hydrocarbon comprises ≥50 wt. % of at least one $C_{2+}$ paraffinic hydrocarbon compound. The first catalyst is produced by exposing the catalyst precursor to a flow of the synthesis hydrocarbon at a temperature in the range of from 500° C. to 750° C., a pressure ≥15 psia (103 kPa), and a space velocity (WHSV) ≥0.1 hr⁻¹. The resulting first catalyst is a multi-component catalyst having dehydrogenation functionality, the first catalyst comprising (i) ≥10 wt. % of at least one inorganic oxide component having a surface area ≥10 m²/g and a pore volume ≥0.1 ml/g, (ii) ≥0.01 wt. % of at least one catalytically active carbonaceous component, and (iii) ≥0.05 wt. % of at least one element selected from Groups 5-11 of the Periodic Table. The process further comprises reacting a feed in the presence of the first catalyst under catalytic dehydrogenation conditions. The feed comprises ≥1 wt. % of a first hydrocarbon and further comprises a second hydrocarbon, wherein the (i) the first hydrocarbon comprises $C_{n+}$ paraffinic hydrocarbon, (ii) the second hydrocarbon comprises $C_{m-}$ hydrocarbon, (iii) n is a positive integer ≥2 and m is a positive integer ≤n−1, and (iv) the feed has a first hydrocarbon:second hydrocarbon molar ratio in the range of from 0.001 to 100. The reaction is carried out under conditions effective for dehydrogenating ≥10 wt. % of the of the $C_{n+}$ paraffinic hydrocarbon of the feed's first hydrocarbon to produce a first product comprising corresponding olefinic hydrocarbon, $C_{m-}$ hydrocarbon, and molecular hydrogen. The process further comprises reacting ≥10 wt. % of the first product's corresponding olefinic hydrocarbon in the presence of a second catalyst under catalytic dehydrocyclization conditions to produce a second product comprising aromatics and additional molecular hydrogen. The second catalyst is a multi-component catalyst having dehydrocyclization functionality and comprising ≥10 wt. % of a molecular sieve component and ≥0.1 wt. % of a dehydrogenation component comprising at least one element selected from Groups 3 to 13 of the Periodic Table.

Other aspects of the invention relate to a process for producing hydrocarbon oligomer. The process includes The process includes producing a first catalyst by contacting a catalyst precursor with a synthesis hydrocarbon. The catalyst precursor comprises at least one element selected from Groups 5-11 of the Periodic Table and at least one inorganic oxide having a surface area ≥10 m²/g and a pore volume ≥0.1 ml/g. The synthesis hydrocarbon comprises ≥50 wt. % of at least one $C_{2+}$ paraffinic hydrocarbon compound. The first catalyst is produced by exposing the catalyst precursor to a flow of the synthesis hydrocarbon at a temperature in the range of from 500° C. to 750° C., a pressure ≥15 psia (103 kPa), and a space velocity (WHSV) ≥0.1 hr⁻¹. The resulting first catalyst is a multi-component catalyst having dehydrogenation functionality, the first catalyst comprising (i) ≥10 wt. % of at least one inorganic oxide component having a surface area ≥10 m²/g and a pore volume ≥0.1 ml/g, (ii) ≥0.01 wt. % of at least one catalytically active carbonaceous component, and (iii) ≥0.05 wt. % of at least one element selected from Groups 5-11 of the Periodic Table. The process further comprises reacting a feed in the presence of the first catalyst under catalytic dehydrogenation conditions. The feed comprises ≥1 wt. % of a first hydrocarbon and further comprises a second hydrocarbon, wherein the (i) the first hydrocarbon comprises $C_{n+}$ paraffinic hydrocarbon, (ii) the second hydrocarbon comprises $C_{m-}$ hydrocarbon, (iii) n is a positive integer ≥2 and m is a positive integer ≤n−1, and (iv) the feed has a first hydrocarbon:second hydrocarbon molar ratio in the range of from 0.001 to 100. The dehydrogenation conditions are effective for dehydrogenating ≥10 wt. % of the of the $C_{n+}$ paraffinic hydrocarbon of the feed's first hydrocarbon to produce a first product comprising corresponding olefinic hydrocarbon, $C_{m-}$ hydrocarbon, and molecular hydrogen. The process further comprises reacting ≥10 wt. % of the first product's corresponding olefinic hydrocarbon in the presence of a second catalyst under catalytic oligomerization conditions including a temperature in the range of from 260° C. to 500° C., a hydrocarbon partial pressure in the range of 50 kPa to 4000 kPa, and a space velocity (WHSV) ≥0.1 hr⁻¹, to produce a second product comprising $C_{5+}$ oligomer derived from the reacted corresponding olefinic hydrocarbon. The second catalyst is a multi-component catalyst having oligomerization functionality and comprising ≥10 wt. % of at least one molecular sieve having a Constraint Index in the range of from 1 to 12 and an α≤250.

BRIEF DESCRIPTION OF THE DRAWINGS

FIG. 1 schematically illustrates certain aspects of the invention which include first and second stage. A feed comprising first and second hydrocarbon is reacted in a reaction zone located within a first stage to produce a first product comprising molecular hydrogen and olefinic hydrocarbon corresponding to the first hydrocarbon. At least a portion of the first product's corresponding olefinic hydrocarbon is reacted in a third stage to produce (i) oligomer containing at least one unit derived from the corresponding olefinic hydrocarbon and/or (ii) aromatic hydrocarbon derived from the corresponding olefinic hydrocarbon.

DETAILED DESCRIPTION

Certain aspects of the invention relate to a hydrocarbon conversion process which includes at least two stages. The feed comprises first and second hydrocarbons. The first hydrocarbon comprises $C_{n+}$ paraffinic hydrocarbon, and the second hydrocarbon comprises $C_{m-}$ hydrocarbon, wherein n is a positive integer ≥2 and m is a positive integer ≤n−1. The feed is introduced into the first stage to catalytic dehydrogenation conditions in the presence of a first catalyst comprising a catalytically active carbonaceous component. The first stage produces a first product comprising molecular hydrogen and olefinic hydrocarbon corresponding to the $C_{n+}$ paraffinic hydrocarbon of the feed's first hydrocarbon. A second stage is provided for converting at least a portion of the corresponding olefinic hydrocarbon to (i) oligomer having at least one unit derived from the corresponding olefinic hydrocarbon and/or (ii) aromatic hydrocarbon. It has been found that the presence of the second hydrocarbon in the feed surprisingly lessens the rate of catalyst deactivation in the first stage and increases selectivity to the corresponding olefinic hydrocarbon. By partially dehydrogenating the first hydrocarbon in the first stage, the second stage exhibits (i) increased hydrocarbon conversion and (ii) produces the oligomer and/or aromatic hydrocarbon with greater selectivity, compared to conventional processes in which the feed is converted in a single stage process using a dehydrocyclization catalyst. The process has also been found to be less selective for undesirable light hydrocarbon byproducts compared to the conventional processes. The invention also encompasses systems and apparatus for carrying out the processes of any of the specified aspects.

Other aspects of the invention relate to a multi-component dehydrogenation catalyst. The catalyst comprises (a) ≥10 wt. % of at least one inorganic oxide component having a surface area ≥10 m²/g and a pore volume ≥0.1 ml/g, (b) 0.01 wt. % to 1 wt. % of at least one catalytically active carbonaceous component, and (c) ≥0.05 wt. % of at least one element selected from Groups 5-11 of the Periodic Table. The catalyst can be produced by contacting the specified catalyst precursor with the specified synthesis hydrocarbon. The catalyst is produced by exposing the catalyst precursor to a flow of the synthesis hydrocarbon at a temperature in the range of from 500° C. to 750° C., a pressure ≥15 psia (103 kPa), and a space velocity (WHSV) in the range of from 0.1 hr$^{-1}$ to 1 hr$^{-1}$.

Definitions

For the purpose of this specification and appended claims, the following terms are defined.

The term "$C_n$" hydrocarbon means hydrocarbon having n carbon atom(s) per molecule, wherein n is a positive integer. The term "$C_{n+}$" hydrocarbon means hydrocarbon having at least n carbon atom(s) per molecule. The term "$C_{n-}$" hydrocarbon means hydrocarbon having no more than n carbon atom(s) per molecule. The term "hydrocarbon" means a class of compounds containing hydrogen bound to carbon, and encompasses (i) saturated hydrocarbon, (ii) unsaturated hydrocarbon, and (iii) mixtures of hydrocarbons, and including mixtures of hydrocarbon compounds (saturated and/or unsaturated), including mixtures of hydrocarbon compounds having different values of n.

The terms "alkane" and "paraffinic hydrocarbon" mean substantially-saturated compounds containing hydrogen and carbon only, e.g., those containing ≤1% (molar basis) of unsaturated carbon atoms. As an example, the term alkane encompasses $C_2$ to $C_{20}$ linear, iso, and cyclo-alkanes.

The term "unsaturate" and "unsaturated hydrocarbon" refer to one or more $C_{2+}$ hydrocarbon compounds which contain at least one carbon atom directly bound to another carbon atom by a double or triple bond. The terms "olefin" and "olefinic hydrocarbon" refer to one or more unsaturated hydrocarbon compound containing at least one carbon atom directly bound to another carbon atom by a double bond. In other words, an olefin is a compound which contains at least one pair of carbon atoms, where the first and second carbon atoms of the pair are directly linked by a double bond. An olefin having a particular number of carbon atoms is the "corresponding olefinic hydrocarbon" of paraffinic hydrocarbon having the same number of carbon atoms. For example, olefinic $C_4$ hydrocarbon (normal butenes and/or isobutene) is the corresponding olefinic hydrocarbon of paraffinic $C_4$ hydrocarbon (butane and/or isobutane). The term "aromatics" and "aromatic hydrocarbon" mean hydrocarbon compounds containing at least one aromatic core.

The term "Periodic Table" means the Periodic Chart of the Elements, as it appears on the inside cover of The Merck Index, Twelfth Edition, Merck & Co., Inc., 1996.

The term "reaction zone" or "reactor zone" mean a location within a reactor, e.g., a specific volume within a reactor, for carrying out a specified reaction. A reactor or reaction stage can encompass one or more reaction zones. More than one reaction can be carried out in a reactor, reactor stage, or reaction zone.

The term "selectivity" refers to the production (on a weight basis) of a specified compound in a catalytic reaction. As an example, the phrase "a light hydrocarbon conversion reaction has a 100% selectivity for aromatic hydrocarbon" means that 100% of the light hydrocarbon (weight basis) that is converted in the reaction is converted to aromatic hydrocarbon. When used in connection with a specified reactant, the term "conversion" means the amount of the reactant consumed in the reaction. For example, when the specified reactant is $C_4$ paraffinic hydrocarbon, 100% conversion means 100% of the $C_4$ paraffinic hydrocarbon is consumed in the reaction. Yield (weight basis) is conversion times selectivity.

The invention includes reacting a feed comprising first and second hydrocarbons in a first stage to selectively convert at least a portion of the first hydrocarbon's $C_{n+}$ hydrocarbon to olefinic hydrocarbon. Representative feeds to the first stage will now be described in more detail. The invention is not limited to these feeds, and this description is not meant to foreclose other feeds within the broader scope of the invention.

Feeds

The feed to the process comprises first and second hydrocarbons, typically ≥1 wt. % of the first hydrocarbon based on the weight of the feed, e.g., ≥5 wt. %, such as ≥10 wt. %, or ≥25 wt. %. The feed typically has a first hydrocarbon:second hydrocarbon molar ratio in the range of from 0.001 to 50, or 0.01 to 10, or 0.1 to 5. It is more typical for the feed to have a first hydrocarbon; second hydrocarbon molar ratio in the range of from, e.g., 0.005 to 0.1, such as 0.01 to 0.05. The first hydrocarbon typically comprises ≥50 wt. % of $C_{n+}$ paraffinic hydrocarbon, e.g., ≥90 wt. %, such as ≥95 wt. %, or ≥99 wt. %, based on the weight of the first hydrocarbon. The second hydrocarbon typically comprises ≥50 wt. % of $C_{m-}$ hydrocarbon, e.g., ≥90 wt. %, such as ≥95 wt. %, or ≥99 wt. %, based on the weight of the second hydrocarbon. Optionally, the feed further comprises diluent, which when present is typically included in the feed in an amount ≤60 wt. % based on the weight of the feed, e.g., ≤40 wt. %, such as ≤30 wt. %, or ≤20 wt. %, or ≤10 wt. %. A feed constituent is diluent when it is substantially non-reactive under the specified reaction conditions in the presence of the specified catalyst, e.g., molecular nitrogen and inert atomic gasses such as argon. The feed can be one that is substantially-free of diluent, e.g., contains ≤1 wt. % of diluent, such as ≤0.1 wt. %, or ≤0.01 wt. %.

The first hydrocarbon typically has a value of n is the range of from 2 to 5, e.g., from 2-4, such as 3 and 4. Suitable first hydrocarbon includes ≥50 wt. % of a first paraffinic hydrocarbon compound, e.g., ≥75 wt. %, such as ≥90 wt. %, or ≥95 wt. %, wherein ≥90 wt. % of any remainder of the first hydrocarbon comprises second and/or third paraffinic hydrocarbon compounds. For example, in one representative first hydrocarbon ("First Hydrocarbon A") the first paraffinic hydrocarbon compound is ethane, the second paraffinic compound is propane, and the third paraffinic compound is one or more butanes. In another representative first hydrocarbon ("First Hydrocarbon B"), the first paraffinic hydrocarbon compound is propane, the second paraffinic hydrocarbon compound is one or more butanes, and the third paraffinic hydrocarbon compound is one or more pentanes. The second and third paraffinic hydrocarbon compounds can be present in any relative amount, although typically the molar amount of second paraffinic hydrocarbon compound is greater than the molar amount of third paraffinic hydrocarbon compound. For example, the molar ratio of paraffinic hydrocarbon compound to third paraffinic hydrocarbon compound can be in the range of from 0.01 to 100, e.g., in the range of from 1 to 75, such as from 2 to 50, or from 3 to 25. Typically, the first hydrocarbon comprises ≤1 wt. % of cyclo-paraffin, e.g., ≤0.1 wt. %, such as ≤0.01 wt. %.

Generally the feed's second hydrocarbon comprises ≥50 wt. % of $C_{m-}$ paraffinic hydrocarbon, based on the weight of the second hydrocarbon, e.g., ≥75 wt. %, such as ≥90 wt. %, or ≥95 wt. %. Typically, m is in the range of from 1 to 3. For example, when the first hydrocarbon is First Hydrocarbon A, the second hydrocarbon comprises methane; and when the first hydrocarbon is Hydrocarbon B, the second hydrocarbon comprises methane and/or ethane. When the second hydrocarbon is a mixture of component hydrocarbon compounds, the relative molar amounts of first component, second component, third component, etc., are typically in inverse proportion to the number of carbon atoms in the component. For example, when the second hydrocarbon comprises methane, ethane, and propane, the relative molar amount of methane is typically greater than the molar amount of ethane, which is typically greater than the molar amount of propane. Typically, the second hydrocarbon comprises ≤1 wt. % of cyclo-paraffin, e.g., ≤0.1 wt. %, such as ≤0.01 wt. %.

Generally, the feed is substantially-free of aromatic hydrocarbon, where substantially-free in this context means an aromatic hydrocarbon content that is ≤1 wt. % based on the weight of the feed, such as ≤0.1 wt. %, or ≤0.01 wt. %, or ≤0.001 wt. %. More typically, the feed is substantially free of (i) $C_{5+}$ hydrocarbon (e.g., $C_{6+}$ hydrocarbon), and/or (ii) oxygenate, and especially oxidant. Typically, the reaction of the first stage does not include oxidative dehydrogenation, e.g., the dehydrogenation of alkanes in the presence of an oxygenate. Although the feed can include olefinic hydrocarbon, typically the feed is substantially free of these. One representative feed comprises ≥50 wt. % of First Hydrocarbon A, with ≥90 wt. % of any remainder of the feed comprising the second hydrocarbon, wherein the second hydrocarbon is methane. For example, the feed can comprise 1 wt. % to 40 wt. % methane, 10 wt. % to 40 wt. % ethane, 20 wt. % to 50 wt. % propane, 20 wt. % to 50 wt. % butanes, and ≤10 wt. % of $C_{5+}$ hydrocarbon such as ≤1 wt. %.

The feed's first and second hydrocarbon can be obtained from one or more sources of hydrocarbon, e.g., from natural hydrocarbon sources such as those associated with producing petroleum, or from one or more synthetic hydrocarbons sources such as catalytic and non-catalytic reactions. Examples of such reactions include, catalytic cracking, catalytic reforming, coking, steam cracking, etc. Synthetic hydrocarbon sources include those in which hydrocarbon within a geological formation has been purposefully subjected to one or more chemical transformations. Optionally, at least a portion of the first hydrocarbon includes $C_{n+}$ paraffinic hydrocarbon that is recycled from effluent of the first and/or second stages. Optionally, at least a portion of the second hydrocarbon includes $C_{m-}$ hydrocarbon that is recycled from effluent of the first and/or second stages.

In certain aspects, the source of the feed's first and/or second hydrocarbon includes natural gas, e.g., raw natural gas ("raw gas"). Natural gas is (i) a mixture comprising hydrocarbon, (ii) primarily in the vapor phase at a temperature of 15° C. and a pressure of 1.013 bar (absolute), and (iii) withdrawn from a geologic formation. Natural gas can be obtained, e.g., from one or more of petroleum deposits, coal deposits, and shale deposits. The natural gas can be one that is obtained by conventional production methods but the invention is not limited thereto. Raw natural gas is a natural gas obtained from a geologic formation without intervening processing, except for (i) treatments to remove impurities such as water and/or any other liquids, mercaptans, hydrogen sulfide, carbon dioxide; and (ii) vapor-liquid separation, e.g., for adjusting the relative amounts of hydrocarbon compounds (particularly the relative amounts of $C_{4+}$ hydrocarbon compounds) in the natural gas; but not including (iii) fractionation with reflux. Conventional methods can be used for removing impurities and/or adjusting the relative amount of hydrocarbon compounds present in the feed, but the invention is not limited thereto. For example, certain components in the natural gas can be liquefied by exposing the natural gas to a temperature in the range of −57° C. to 15° C., e.g., −46° C. to 5° C., such as −35° C. to −5° C. At least a portion of the liquid phase can be separated in one or more vapor-liquid separators, e.g., one or more flash drums. One suitable raw natural gas comprises 3 mole % to 70 mole % methane, 10 mole % to 50 mole % ethane, 10 mole % to 40 mole % propane, and 5 mole % to 40 mole % butanes and 1 mole %6 to 10 mole % of total $C_5$ to $C_9$ hydrocarbon. In certain aspects, ≥50 wt. % of the feed comprises natural gas, such as raw natural gas, e.g., ≥75 wt. %, or ≥90 wt. %, or ≥95 wt. %. When the feed comprises natural gas, the feed's first hydrocarbon includes at least a portion of the natural gas's ethane, propane, butanes, and optionally pentanes (n=2) and the feed's second hydrocarbon comprises at least a portion of the natural gas's methane (m=1).

Any form of raw gas can be used as a source material, although the raw gas is typically one or more of (i) gas obtained from a natural gas well ("Gas Well", Non-associated", or "Dry" gas), (ii) natural gas obtained from a condensate well ("Condensate Well Gas"), and (iii) casing head gas ("Wet" or "Associated" gas). Table 1 includes typical raw gas compositional ranges (mole %) and, parenthetically, typical average composition (mole %) of certain raw gasses.

TABLE 1

| Component | Associated Gas | Dry Gas | Condensate Well Gas |
|---|---|---|---|
| $CO_2$ | 0-50 (0.63) | 0-25 (0) | 0-25 (0) |
| $N_2$ | 0-50 (3.73) | 0-25 (1.25) | 0-25 (0.53) |
| $H_2S$ | 0-5 (0.57) | 0-5 (0) | 0-5 (0) |
| $CH_4$ | 0-80 (64.48) | 0-97 (91.01) | 0-98 (94.87) |
| $C_2H_6$ | 5-20 (11.98) | 2-10 (4.88) | 1-5 (2.89) |
| $C_3H_8$ | 2-10 (8.75) | 0.5-5 (1.69) | 0.1-5 (0.92) |
| i-butane | 0.1-5 (0.93) | 0.05-1 (0.14) | 0.1-5 (0.31) |
| n-butane | 1-5 (2.91) | 0.05-2 (0.52) | 0.05-2 (0.22) |
| i-pentane | 0.05-2 (0.54) | 0.01-1 (0.09) | 0.01-1 (0.09) |

In certain aspects, the feed comprises % 75 wt. % Associated Gas (n=2, m=1), based on the weight of the feed, e.g., ≥90 wt. %, or ≥95 wt. %. Associated Gas is typically found with petroleum deposits, e.g., dissolved in the oil or as a free "gas cap" above the oil in a reservoir.

Advantageously, when the feed is derived from a methane-containing source such as natural gas, complex and costly processes for separating methane from other light hydrocarbon in the source can be avoided. The invention thus offers significant advantages in remote or under-developed locations, where the lack of a pipeline or natural gas production infrastructure, may result in significant quantities of light hydrocarbon ($C_1$ to $C_4$) resources being burned as fuel rather than being recovered. Small scale plants using the present process would allow effective recovery of these light hydrocarbon resources as liquid hydrocarbons.

The feed is conducted to a first stage, where it is reacted in the presence of at least one first stage catalyst in at least one reaction zone operating under catalytic dehydrogenation conditions. The reaction converts at least a portion of the $C_{n+}$ paraffinic hydrocarbon in the feed's first hydrocarbon to corresponding olefinic hydrocarbon. Certain aspects of the first stage will now be described in more detail. The invention is not limited to these aspects, and this description is not meant to foreclose other aspects of the first stage within the broader scope of the invention.

First State

Referring to FIG. 1, at least one of the specified feeds 100 is conducted to reaction zone 110, the reaction zone being typically located within a reactor vessel (not shown). The reaction zone includes at least one first catalyst having a catalytically active carbonaceous component. The feed is reacted in reaction zone 110 in the presence of the first catalyst under catalytic dehydrogenation conditions sufficient for converting to corresponding olefinic hydrocarbon at least a portion of the $C_{n+}$ paraffinic hydrocarbon of the feed's first hydrocarbon. A first product is conducted away from reaction zone 110 via conduit 130, the first product comprising molecular hydrogen, at least a portion of the corresponding olefinic hydrocarbon, $C_{m-}$ hydrocarbon, and any unreacted first hydrocarbon. The first catalyst has at least three components. The first component comprises inorganic oxide having a surface area ≥10 $m^2/g$ and a pore volume ≥0.1 ml/g. The second component comprises at least one catalytically active carbonaceous material. The third component comprises at least one element selected from Groups 5-11 of the Periodic Table. Generally, the catalyst comprises ≥10 wt. % of the first component, ≥3 wt. % of the second component, and ≥0.01 wt. % of the third component, the weight percents being based on the weight for the first catalyst. Suitable catalysts include those described in P.C.T. Patent Application Publication No. WO2010/140005, which is incorporated by reference herein in its entirety. Certain first, second and third components will now be described in more detail. The invention is not limited to these, and this description is not meant to foreclose other components and component compositions within the broader scope of the invention.

The first component of the first catalyst comprises inorganic oxide, e.g., one or more of silica, alumina, silica-alumina, titania, zirconia, ceria, yttria, and magnesia. In certain aspects, the first component comprises ≥90 wt. % of one or more of silica, alumina, and silica-alumina, e.g., ≥95 wt. %, such as ≥99 wt. %. For example, the first component can be silica and/or alumina. Generally, the catalyst comprises ≥15 wt. % of the first component, e.g., ≥20 wt. %. The first component's inorganic oxide can be one that has porosity, e.g., one or more molecular sieves. Typically, the first component has a surface area ≥25 $m^2/g$, e.g., ≥50 $m^2/g$, such as ≥75 $m^2/g$, or in the range of from 50 $m^2/g$ to 500 $m^2/g$, such as 75 $m^2/g$ to 400 $m^2/g$. The first component typically has a pore volume ≥0.1 ml/g, e.g., ≥0.4 ml/g, such as in the range of from 0.1 ml/g to 1 ml/g, or 0.4 ml/g to 0.8 ml/g.

The second component of the first catalyst comprises at least one catalytically active carbonaceous material. In certain aspects, the first catalyst comprises ≥5 wt. % of the second component, such as ≥10 wt. %. The catalytically active carbonaceous material can include a structurally ordered deposit of carbon, e.g., carbon in the form of a nanostructure. Suitable carbon nanostructures include one or more of carbonaceous nanofibers, carbonaceous nanotubes, and other ordered nanoscale forms of carbon. The catalytically active carbonaceous material can be supported by the first catalyst's inorganic oxide component, but this is not required. In certain aspects, the catalytically active carbonaceous material is unsupported. When the catalytically active carbonaceous material is supported, the support can be, e.g., (i) carbon, such as a non-catalytically active form of carbon, and/or (ii) an inorganic support, such as the first catalyst's first and/or second components. When the catalytically active carbonaceous material is not supported, it can be, e.g., composited with the first catalyst's first and/or second components. Conventional methods can be utilized for producing supported or composited catalytically active carbonaceous material, but the invention is not limited thereto. The catalytically active carbonaceous material can be formed in-situ (e.g., in the reactor under the specified catalytic dehydrogenation conditions), but this is not required. For example, in certain aspects the catalytically active carbonaceous material is pre-formed (ex-situ), with the catalytically active carbonaceous material then added to, composited with, or deposited on the first catalyst or the first and/or third components thereof.

In particular aspects, the catalytically active carbonaceous component (i) comprises ≥90 wt. % of carbon and/or carbide, and (ii) has the morphology of one or more of (A) one or more graphene layers, (B) a plurality of nanotubes, and (C) a plurality of nanofibers. The specified carbonaceous component is "catalytically active" in the sense that (i) it can actively catalyze the dehydrogenation of the specified $C_{n+}$ olefin under the specified process conditions of the first stage and/or (ii) it modifies the first catalyst's first and/or third component in a way that (A) increases the first catalyst's activity for the dehydrogenation reaction and/or (B) increases the first catalyst's selectivity for the corresponding olefinic hydrocarbon.

The third component typically comprises ≥90 wt. % of at least one element (or compound thereof) selected from Groups 5-11 of the Periodic Table, e.g., ≥95 wt. %, such as ≥99 wt. %. For example, the third component can comprise at least one transition metal or transition metal compound, such as one or more of V, Cr, Mn, Fe, Co, Mo, Ni, Au, Pt, Pd, Ru and Rh. The third component can include one or more of the specified elements in elemental form. Alternatively or in addition, the third component can include one or more compounds which include at least one of the specified elements, e.g., one or more of oxide (including mixed oxide where the metal forms more than one oxide), carbonate, nitrate, sulfate, sulfide or hydroxide. The specified element can be present in one or more than one oxidation state, for example as a mixture of elemental metal and a metal oxide, or more than one metal oxide.

The third component can be supported, e.g., by the first component and/or another suitable support such as the second component, but this is not required. In certain aspects, the third component is not supported by the first and/or third component, but instead is composited with the other components of the first catalyst. When a supported third component is desired, it can be produced by any convenient method, e.g., precipitation, co-precipitation, deposition precipitation, and impregnation. One or more oxides of the specified elements can be formed by calcination, for example. Conventional methods are suitable for applying the third component to a support, but the invention is not limited thereto.

The catalyst typically comprises ≥0.01 wt. % of the third component, e.g., ≥0.05 wt. %, such as ≥1 wt. %, or ≥3 wt. %, or ≥5 wt. %. For example, the catalyst can comprise 0.01 wt. % to 50 wt. % of the third component. e.g., in the range of from 0.1 wt. % to 10 wt. %, such as in the range of 0.5 wt. % to 10 wt. %, or 0.5 wt. % to 5 wt. ° %. In certain aspects, the first catalyst comprises ≥1 wt. % of the specified element or elements, such as ≥2.5 wt. %, or ≥5 wt. %. More particularly, the catalyst can comprise 0.1 wt. % to 50 wt. % of the specified element or elements, e.g., in the range of from 0.1 wt. % to 10 wt. %, such as in the range of 0.5 wt. % to 10 wt. %, or 0.5 wt. % to 5 wt. %. These ranges are applicable whether the third component comprises one or more of the specified elements (i) in elemental form, (ii) in the form of one or more compounds of the specified elements or combination of elements, or (iii) in both elemental and compound form. Those skilled in the art will appreciate that the amount of third component will depend to some extent on the element(s) selected and on their chemical form. More particularly, a lesser amount within the specified range is typically used with metals having greater dehydrogenation activity, such as Pt.

The catalyst can be produced by any convenient method. Conventional methods can be used, such as those described in P.C.T. Patent Application Publication No. WO2010/140005, but the invention is not limited thereto. For example, the catalyst can be produced in situ from a catalyst precursor in the presence of a synthesis feed, e.g., a synthesis hydrocarbon, under catalyst production conditions for a time sufficient to form the first catalyst from the catalyst precursor. Typically, this includes forming the specified catalytically active carbonaceous component, e.g., on, in, or proximate to the catalyst precursor. Process conditions used during in-situ production of the first catalyst can be selected from among those process conditions, e.g., temperature, pressure, and space velocity, used for producing the first product.

In certain aspects, the first catalyst is produced by exposing a catalyst precursor to a synthesis hydrocarbon, the synthesis hydrocarbon comprising ≥50 wt. % of at least one $C_{2+}$ paraffinic hydrocarbon compound, e.g., ≥75 wt. %, such as ≥90 wt. %, or ≥95 wt. %. The $C_{2+}$ paraffinic hydrocarbon can be selected from among those specified in connection with the feed. The catalyst precursor can comprise at least one element selected from Groups 5-11 of the Periodic Table and at least one inorganic oxide having a surface area ≥10 m$^2$/g and a pore volume ≥0.1 ml/g. For example, the catalyst precursor can comprise ≥10 wt. % of the first component specified in connection with the first catalyst and ≥0.05 wt. % of the third component specified in connection with the first catalyst. Catalyst precursors described in P.C.T. Patent Application Publication No. WO2010/140005 are suitable, but the invention is not limited thereto. The first catalyst can be produced from the catalyst precursor by exposing the catalyst precursor to a flow of the synthesis hydrocarbon at a temperature ≥400° C., typically ≥500° C., e.g., ≥600° C., such as ≥700° C. For example, the catalyst precursor can be exposed to the synthesis hydrocarbon flow at a temperature in the range of from 650° C. to 750° C., such as 680° C. to 730° C. Typically the catalyst precursor is exposed to the specified temperature and flow conditions for a time sufficient for forming a catalytically effective amount of the specified second component. For example, the catalyst precursor can be exposed to the specified temperature and flow conditions for a time sufficient to form the second component in an amount ≥0.1 wt. % of the first catalyst, e.g., ≥1 wt. %, or ≥3 wt. %, or ≥5 wt. %, such as in the range of from 0.01 wt. % to 10 wt. %, or 1 wt. % to 5 wt. %. Typically, the flow of the synthesis hydrocarbon is carried out in the specified temperature range at a pressure ≥15 psia (103 kPa) and a space velocity (WHSV) ≥0.1 hr$^{-1}$. Those skilled in the art will appreciate that the time duration needed to form the first catalyst from the catalyst precursor will depend on the selected synthesis conditions, e.g., one or more of temperature, pressure, and space velocity. Typically, this time duration is ≥0.1 hour, e.g., ≥1 hour, or ≥10 hours, such as in the range of from 1 hour to 100 hours, or 5 hours to 25 hours.

After a catalytically effective amount of the first catalyst is provided to the first stage, e.g., by forming it in-situ, the flow of synthesis hydrocarbon is curtailed or halted and a flow of the specified first mixture is established. Optionally, one or more first catalyst pre-treatments can be carried out, e.g., calcining, sulfidation, etc., before establishing feed flow. Referring again to FIG. 1, the specified feed is reacted in reaction zone 110 in the presence of the first catalyst under catalytic dehydrogenation conditions for a time sufficient for converting to corresponding olefinic hydrocarbon at least a portion of the $C_{n+}$ paraffinic hydrocarbon of the feed's first hydrocarbon.

The catalytic dehydrogenation conditions in the first stage can include a temperature ≥400° C., e.g., ≥500° C., such as in the range of from 650° C. to 750° C. Particularly for a first hydrocarbon having a value of n≥3, e.g., First Hydrocarbon B, the catalytic dehydrogenation conditions in the first stage can include a temperature in the range of from 400° C. to 650° C., e.g., from 450° C. to 625° C. Pressure is typically ≥15 psia (103 kPa), and space velocity (WHSV) is typically ≥0.1 hr$^{-1}$. Conditions in the first stage are typically selected to provide (i)≤25% conversion of the feed's second hydrocarbon, such as ≤10%, or ≤5%, or ≤1% and (ii) ≥25% conversion of the feed's first hydrocarbon (particularly conversion of the $C_{2+}$ paraffinic hydrocarbon component thereof), e.g., ≥50%, or ≥75 wt. For example, when the feed's first hydrocarbon includes First Hydrocarbon A and the feed's second hydrocarbon includes methane (e.g., a feed which comprises raw natural gas), process conditions in the first stage typically include a temperature in the range of from 500° C. to 750° C., e.g., 500° C. to 650° C., such as 525° C. to 625° C.; a pressure in the range of from 15 psia (103 kPa) to 80 psia (522 kPa); and a space velocity (WHSV) ≥0.1 hr$^{-1}$. Particularly when the first catalyst's third component comprises one or more of Ga, In, and Zn (and/or one or more oxide thereof), such conditions typically result in a methane conversion ≤5% and a First Hydrocarbon A conversion ≥50%. As another example, when the first hydrocarbon includes First Hydrocarbon B and the second hydrocarbon includes ethane and optionally methane, process conditions in the first stage typically include a temperature in the range of from 450° C. to 605° C., e.g., 450° C. to 575° C., such as 450° C. to 550° C.; a pressure in the range of from 30 psia (207 kPa) to 80 psia (522 kPa); and a space velocity (WHSV) ≥0.1 hr$^{-1}$. Particularly when the first catalyst's third component comprises one or more of Ga, In, and Zn (and/or one or more oxide thereof), such conditions typically result in a methane (when present) conversion ≤1%, an ethane conversion ≤5%, and a First Hydrocarbon B conversion ≥50%.

Conventional fixed, moving, and/or fluidized beds can be used in reaction zone 110, but the invention is not limited thereto. In the reactor beds of stages 1 and 2, the temperature drop across a reactor bed is typically in the range of from 20° C. to 200° C., e.g., in the range of from 50° C. to 150° C.

It has been surprisingly found that improved conversion of the feed's first hydrocarbon and improved selectivity to the corresponding olefin hydrocarbon are achieved over conventional catalysts containing a catalytically active carbonaceous component. And contrary to expectations, these improvements are achieved even when the feed is substantially free of diluent such as molecular nitrogen. While not wishing to be bound by any theory or model, it is believed that the feed's second hydrocarbon functions as an unconsumed co-reactant in the first stage, in addition to or instead of any dilution effect that it may provide. The term "unconsumed" means little or no consumption on a net basis. For example, even though some of the feed's second hydrocarbon is converted, e.g., to coke or coke precursors, additional second hydrocarbon is produced, e.g., by hydrogenolysis or cracking of the first hydrocarbon. An advantage of the process is that efficient conversion of the feed's first hydrocarbon can be be carried out under conditions that are significantly milder than those of conventional processes, which lessens selectivity for undesired light saturated hydrocarbon. Advantageously, the process can be carried out using a first catalyst that contains much less of the catalytically active carbonaceous phase (the first catalyst's second component) than is needed in conventional processes. For example, in certain aspects the first catalyst comprises an amount of the second component in the range of from 0.01 wt. % to 1 wt. %, e.g., 0.01 to 0.1 wt. %, based on the weight of the first catalyst. Using a first catalyst which comprises the second component in these ranges is believed to increase access of hydrocarbon molecules in the feed to the dehydrogenation metals of the third component. It is believed that this provides at least part of the enhanced feed conversion. These enhancements also lessen the need for first catalyst regeneration, resulting in increased run lengths. The desired amount of second component can be achieved, e.g., by adjusting space velocity (WHSV) when exposing the catalyst precursor to the synthesis mixture, e.g., in a space velocity range of from 0.1 hr$^{-1}$ to 2 hr$^{-1}$, or 0.1 hr$^{-1}$ to 1 hr$^{-1}$, or 0.15 hr$^{-1}$ to 0.5 hr$^{-1}$.

Returning to FIG. 1, a first product is conducted away from reaction zone 110 via conduit 130, the first product comprising molecular hydrogen, at least a portion of the corresponding olefinic hydrocarbon, $C_{m-}$ hydrocarbon, and any unreacted first hydrocarbon. When the first stage is operated using the specified feed, the specified first catalyst, and the specified process conditions, selectivity to olefinic hydrocarbon compounds corresponding to the $C_{2+}$ paraffinic hydrocarbon compounds included in the feed is typically ≥50%, e.g., ≥75%, such as ≥90%, or ≥95%. Selectivity to aromatic hydrocarbon is typically ≤15%, e.g., ≤10%, such as ≤1%. Generally, the first product is substantially free of aromatic hydrocarbon. Selectivity to non-catalytically active carbonaceous material, e.g., catalyst coke and/or catalyst coke precursors is typically ≤15%, e.g., ≤10%. Selectivity to hydrocarbon compounds having fewer carbon atoms than those of the feed's first hydrocarbon is typically ≤5%, e.g., ≤1%, such as ≤0.5%. Consequently, the $C_{m-}$ hydrocarbon present in the first product is primarily unreacted second hydrocarbon of the feed. Typically, ≥90 wt. % of the first product's $C_{m-}$ hydrocarbon is unreacted second hydrocarbon, e.g., ≥95 wt. %, such as ≥99 wt. %. Typically, the corresponding olefinic hydrocarbon comprises corresponding monoolefin, e.g., ≥75 wt. % of corresponding monoolefin, such as ≥90 wt. %, or ≥99 wt. %. In certain aspects:

a. the feed's first hydrocarbon comprises a mixture of ethane, propane, and butanes; the feed's second hydrocarbon comprises methane; and the first and second hydrocarbon are directly obtained from a raw natural gas comprising ≥1 wt. % methane, 10 wt. % to 40 wt. % ethane, 20 wt. % to 50 wt. % propane, and 20 wt. % to 50 wt. % butanes, and b. the first product comprises ≥20 wt. % of corresponding olefinic hydrocarbon, the corresponding olefinic hydrocarbon including one or more of ethylene, propylene, and butylenes.

Continuing with reference to FIG. 1, one or more optional separations 140 can be used downstream of reaction zone 110. Separations 140 can be used, e.g., for removing from the first product one or more of (i) at least a portion of the first product's molecular hydrogen, (ii) at least a portion of any $C_{m-}$ hydrocarbon in the first product, beyond that which might be needed in the second stage separating saturated, and (iii) at least a portion of any unreacted first hydrocarbon. These can be removed from stage 140 as components of an extract, which is withdrawn via one or more conduits represented by line 150. Following extract removal, the remainder of the first product typically comprises ≥50 wt. % of the first product's corresponding olefinic hydrocarbon, e.g., ≥75 wt. %, such as ≥90 wt. %. A majority of the remainder e.g., ≥90 wt. %, or substantially all of the remainder, is conducted away as raffinate via conduit 160. Conventional separations can be used in stage 140, but the invention is not limited thereto. The raffinate typically has a corresponding olefinic hydrocarbon content that is at least 1.1 times greater than that of the first product, e.g., ≥1.5 times, such as ≥2 times, or ≥5 times, or ≥10 times. In certain aspects, the raffinate comprises ≥25 wt. % of olefinic hydrocarbon, based on the weight of the raffinate, with ≥90 wt. % of the remainder of the raffinate comprising normal and iso-paraffinic hydrocarbon. Typically, the raffinate is substantially free of (i) molecular hydrogen, (ii) cyclo paraffin, and (iii) aromatic hydrocarbon.

Since the dehydrogenation reaction of the first stage is typically endothermic, it can be desirable to subject the raffinate to one or more heat transfers 170 to provide at least a portion of the heat needed to carry out the dehydrocyclization reaction of the second stage. Any convenient heating method can be used, including conventional heat transfer methods (direct and/or indirect), but the invention is not limited thereto. For example, at least a portion of the transferred heat can be produced by (i) combusting paraffinic hydrocarbon (such as methane) separated from the first product and/or (ii) electric heaters powered by electricity produced using paraffinic hydrocarbon (such as methane) separated from the first product. Heated raffinate can be conducted away from heat transfer 170 to the second stage via conduit 180. Certain aspects of the second stage will now be described in more detail. The invention is not limited to these aspects, and this description is not meant to foreclose other forms of dehydrocyclization of the first product or raffinate thereof within the broader scope of the invention.

Second Stage

Continuing with reference to FIG. 1, heated raffinate is conducted via conduit 180 to reaction zone 190, the reaction zone being typically located within a reactor vessel (not shown). At least two different kinds of reaction can be carried out using raffinate 170: oligomerization and dehydrocyclization. Accordingly, in certain aspects of the invention reaction zone 190 includes a second catalyst having dehydrocyclization functionality for producing a second product comprising aromatic hydrocarbon. The aromatic hydrocarbon includes at least a portion of the carbon atoms of the corresponding olefinic hydrocarbon in the first product, e.g., carbon atoms of the separated portion of the corresponding olefinic hydrocarbon contained in the raffinate. In other aspects, reaction zone 250 is used instead of reaction zone 190. Reaction zone 250 includes a third catalyst having oligomerization functionality for producing a third product comprising oligomer of order two or greater, the oligomer having at least one unit derived from corresponding olefinic hydrocarbon in the first product, e.g., derived from the separated portion of the corresponding olefinic hydrocarbon contained in the raffinate. In related aspects, the second stage contains reaction zone 190 and 250, these zones being operated in parallel as shown in FIG. 1. Stage 2 optionally includes valve means, e.g., $V_1$ and $V_2$, for controlling the relative amount of heated raffinate conducted to reaction zone 190 (for dehydrocyclization) and/or reaction zone 250 (for oligomerization). In these aspects, (i) a first portion of corresponding olefinic hydrocarbon of the heated raffinate can be conducted to reaction zone 190, which contains the second catalyst and is operated under conditions effective for converting to aromatic hydrocarbon at least a portion of the corresponding olefinic hydrocarbon in the heated raffinate and (ii) a second portion of the corresponding olefinic hydrocarbon of the heated raffinate is conducted to reaction zone 250, which contains the third catalyst and is operated under conditions effective for producing a third product comprising oligomer containing at least one unit derived from the corresponding olefinic hydrocarbon. A second product is conducted away from reaction zone 190 via conduit 200, the second product comprising aromatic hydrocarbon and additional molecular hydrogen. A third product, comprising at least a portion of the oligomer is conducted away from reaction zone 250 via conduit 260. The second and third catalysts, the oligomerization, and the dehydrocyclization will now be described in more detail.

Second and Third Catalysts

The second and third catalysts each comprise a molecular sieve component, e.g., in an amount ≥20 wt. %, based on the weight of the catalyst, e.g., ≥25 wt. %, such as ≥30 wt. %, or in the range of from 30 wt. % to 99.9 wt. %. The molecular sieve component can include aluminosilicate, e.g., ≥90 wt. % of at least one aluminosilicate. The aluminosilicate can be an un-substituted aluminosilicate, a substituted aluminosilicate, or a combination thereof. Typically, the aluminosilicate incudes zeolitic aluminosilicate, e.g., ≥90 wt. % of at least one zeolite based on the weight of the aluminosilicate.

The molecular sieve component typically comprises ≥90 wt. % of one or more of the specified molecular sieves, e.g., ≥95 wt. %. In certain aspects, the molecular sieve component comprises at least one zeolite molecular sieve, e.g., ≥90 wt. % zeolite, such as ≥95 wt. %, based on the weight of the molecular sieve component. Although, the molecular sieve component can consist essentially of or even consist of zeolite, in alternative aspects the zeolite(s) is present in the molecular sieve component in combination with other (e.g., non-zeolitic) molecular sieve. The zeolite can be one that is in hydrogen form, e.g., one that has been synthesized in the alkali metal form, but is then converted from the alkali to the hydrogen form.

Examples of suitable zeolites include ZSM-5, ZSM-11, ZSM-5/ZSM-11 intermediate, ZSM-12, ZSM-23, ZSM-35, ZSM-48, including and mixtures and intermediates thereof such as ZSM-5/ZSM-11 admixture. ZSM-5 is described in U.S. Pat. No. 3,702,886 and Re. 29,948. ZSM-11 is described in U.S. Pat. No. 3,709,979. A ZSM-5/ZSM-11 intermediate structure is described in U.S. Pat. No. 4,229,424. ZSM-12 is described in U.S. Pat. No. 3,832,449. ZSM-23 is described in U.S. Pat. No. 4,076,842. ZSM-35 is described in U.S. Pat. No. 4,016,245. ZSM-48 is described in U.S. Pat. No. 4,234,231.

In other aspects, the molecular sieve component of the second and/or third catalyst comprises at least one molecular sieve of the MCM-22 family, e.g., MCM-22 alone or in combination with other molecular sieve such as one or more of the specified zeolites. As used herein, the term "molecular sieve of the MCM-22 family" (or "material of the MCM-22 family" or "MCM-22 family material" or "MCM-22 family zeolite") includes one or more of:

(i) molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);

(ii) molecular sieves made from a common second degree building block, being a 2-dimensional tiling of such MWW framework topology unit cells, forming a monolayer of one unit cell thickness, preferably one c-unit cell thickness;

(iii) molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and (iv) molecular sieves made by any regular or random 2-dimensional or 3-dimensional combination of unit cells having the MWW framework topology.

The MCM-22 family include those molecular sieves having an X-ray diffraction pattern including d-spacing maxima at 12.4±0.25, 6.9±0.15, 3.57±0.07 and 3.42±0.07 Angstrom. The X-ray diffraction data used to characterize the material are obtained by standard techniques using the K-alpha doublet of copper as incident radiation and a diffractometer equipped with a scintillation counter and associated computer as the collection system.

Materials of the MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), and mixtures thereof. Related zeolite UZM-8 is also suitable for use as the molecular sieve component.

In certain aspects, the second and/or third catalyst further comprises at least one rare earth element, e.g., in an amount ≥0.01 wt. % based on the weight of the catalyst, such as ≥0.1 wt. %, or ≥1.0 wt. %. Suitable rare earth elements include one or more of Sm, Nd, Pr, Ce, and La. It has been found that when the second catalyst includes one or more rare earth elements, that the oligomerization and/or dehydrocyclization reactions exhibit a decreased selectivity for conversion of the corresponding olefinic hydrocarbon to catalyst coke. When used, the rare earth element can be base-exchanged with the catalyst's molecular sieve and/or impregnated into the catalyst's molecular sieve. Conventional base-exchange and impregnation methods can be used, but the invention is not limited thereto.

Besides the molecular sieve component, the second and/or third catalyst optionally further comprises a matrix component, e.g., one or more inorganic binders. A matrix component can be used, e.g., to make the catalyst more resistant to the temperatures and other conditions employed in the conversion reaction. The amount of matrix component is not critical. When present, the amount of matrix component is typically in the range of 0.01 times the weight of the molecular sieve component to about 0.9 times the weight of the molecular sieve component, e.g., in the range of 0.02 to 0.8. The matrix component can include active materials, such as synthetic or naturally occurring zeolites. Alternatively or in addition, the matrix component can include clays and/or oxides such as alumina, silica, silica-alumina, zirconia, titania, magnesia or mixtures of these and other oxides. The matrix component can include naturally occurring materials and/or materials in the form of gelatinous precipitates or gels including mixtures of silica and metal oxides. Clays may also be included with the oxide type binders to modify the mechanical properties of the catalyst or to assist in its manufacture. Alternatively or in addition, the matrix component can include one or more substantially inactive materials. Inactive materials suitably serve as diluents to control the amount of conversion so that products may be obtained economically and orderly without employing other means for controlling the rate of reaction. These materials may be incorporated into naturally occurring clays, e.g., bentonite and kaolin, to improve thermal and strength properties (e.g., crush strength) of the catalyst under catalytic conversion conditions.

Particular features of the second and third catalysts will now be described in more detail.

Second Catalyst

The second catalyst comprises ≥10 wt. % of a molecular sieve component and ≥0.005 wt. % of a dehydrogenation component. When the molecular sieve component and dehydrogenation component together comprise less than 100 wt. % of the catalyst, ≥90 wt. % of the remainder of the catalyst can comprise the specified matrix component, such as ≥99 wt. % of the remainder.

When the second catalyst's molecular sieve component comprises aluminosilicate, e.g., zeolite, the aluminosilicate can be in a form where at least a portion of its original metal has been replaced, e.g., by ion exchange, with other suitable metal (typically metal cation) of Groups 1-13 of the Periodic Table. For example, zeolite of the second catalyst can include those in which at least part of the aluminum is replaced by a different trivalent metal, such as gallium or indium. Alternatively or in addition to the previously specified zeolites, the second catalyst's molecular sieve component can comprise ZSM-22. ZSM-22 is described in U.S. Pat. No. 4,556,477. Typically the zeolite of the second catalyst is one having a medium pore size and a Constraint Index of 2-12 (as defined in U.S. Pat. No. 4,016,218).

Optionally, the zeolite of the second catalyst is one comprising at least one set of pores of substantially uniform size extending through the molecular sieve, wherein geometric mean of the cross-sectional dimensions of each of the sets of pores is ≥5 Å, or ≥5.3 Å, e.g., ≥5.4 Å such as ≥5.5 Å, or in the range of 5 Å to 7 Å, or 5.4 Å to 7 Å. ZSM-5 and/or ZSM-12 are suitable, particularly H-ZSM-5. For example, the molecular sieve component can comprise ≥90 wt. % of (A) ZSM-5 and/or (B) ZSM-12, based on the weight of the molecular sieve component, e.g., ≥95 wt. % of H-ZSM-5.

When the molecular sieve component comprises at least one aluminosilicate, e.g., at least one zeolite, the aluminosilicate's silica:alumina ratio (substantially the same as the aluminosilicate's Si:Al$_2$ atomic ratio) is typically ≥2, e.g., in the range of from 5 to 100. The silica:alumina ratio is meant to represent the Si:Al$_2$ atomic ratio in the rigid anionic framework of the crystalline aluminosilicate. In other words, aluminum in (i) any matrix or binder or (ii) in cationic or other form within the crystalline aluminosilicate's channels is excluded from the silica:alumina ratio. Alternatively or in addition, the catalyst can be made more resistant to deactivation (and increase aromatic hydrocarbon yield) by including phosphorous with the molecular sieve component. Conventional methods can be utilized for adding phosphorous, but the invention is not limited thereto. When used, the amount of phosphorous is typically ≥1 wt. % based on the weight of the molecular sieve component. For example, when the molecular sieve component comprises aluminosilicate, the phosphorous:aluminum atomic ratio can be in the range of from 0.01 to 1. Zeolite having a higher silica:alumina ratio can be utilized when a lower catalyst acidity is desired, e.g., in the range of from 44 to 100, such as from 50 to 80, or 55 to 75.

Alternatively or in addition to any phosphorous added to or impregnated into the second catalyst's molecular sieve component, the optional matrix component can be one which includes phosphorous. Suitable phosphorous-containing matrices are disclosed in U.S. Pat. No. 5,026,937, which is incorporated by reference herein in its entirety. The matrix component is optional. In certain aspects, the second catalyst is substantially-free of matrix, e.g., contains ≤1 wt. % of matrix, such as ≤0.1 wt. %. In particular, the second catalyst can be substantially free of binder, e.g., contains ≤1 wt. % of binder, such as ≤0.1 wt. %. For example, the second catalyst's molecular sieve component can comprises ≥95 wt. % of substantially binder-free bound molecular sieve, e.g., ≥95 wt. % of substantially binder-free ZSM-5, and in particular small crystal H-ZSM-5. Small crystal ZSM-5 and the method for determining molecular sieve crystal size are disclosed in U.S. Pat. No. 6,670,517, which is incorporated by reference herein in its entirety.

In addition to the molecular sieve component and optional matrix component, the second catalyst comprises ≥0.005 wt. % of a dehydrogenation component, based on the weight of the catalyst, e.g., at least one dehydrogenation metal. For example, the dehydrogenation component can comprise one or more neutral metals selected from Groups 3 to 13 of the Periodic Table of the Elements, such as one or more of Ga, In, Zn, Cu, Re, Mo, W, La, Fe, Ag, Pt, and Pd, and/or one or more oxides, sulfides and/or carbides of these metals. Typically, the dehydrogenation component comprises ≥90 wt. % of the one or more of the specified dehydrogenation metals and/or oxide thereof, e.g., ≥95 wt. %, or ≥99 wt. %. For example, the dehydrogenation component can comprise ≥90 wt. % of (A) Ga and/or (B) Zn, including oxides thereof. Typically, the second catalyst comprises ≥0.01 wt. % of the dehydrogenation component, based on the weight of the catalyst. For example, the catalyst can comprise ≥0.1 wt. % of the dehydrogenation component, such as ≥0.5 wt. %, or ≥1 wt. %. Those skilled in the art will appreciate that when the dehydrogenation component comprises one or more metals of greater catalytic dehydrogenation activity, e.g., Pt, and/or Pd, a lesser amount of dehydrogenation component is needed, e.g., in the range of 0.005 wt. % to 0.1 wt. %, based on the weight of the catalyst, such as 0.01 wt. % to 0.6 wt. %, or 0.01 wt. % to 0.05 wt. %. When the dehydrogenation component comprises one or more metals of lesser dehydrogenation activity, e.g., one or more of Ga, In, Zn, Cu, Re, Mo, and W, a greater amount of dehydrogenation component is needed, e.g., in the range of 0.05 wt. % to 10 wt. %, based on the weight of the catalyst, such as 0.1 wt. % to 5 wt. %, or 0.5 wt. % to 2 wt. %.

The dehydrogenation component can be provided on, in, or proximate to the second catalyst in any manner, for example by conventional methods such as impregnation or ion exchange of the molecular sieve with a solution of a compound of the relevant metal, followed by conversion of the metal compound to the desired form, namely neutral metal, oxide, sulfide and/or carbide. As specified in connection with the molecular sieve component, at least part of the dehydrogenation metal may also be present in the crystalline framework of the molecular sieve. For one representative catalyst, (i) the dehydrogenation component comprises ≥95 wt. % of (A) Ga and/or (B) Zn, and (ii) the first molecular sieve component comprises ≥95 wt. % of H-ZSM-5.

In certain aspects, the second catalyst's dehydrogenation component comprises ≥99 wt. % of one or more of Ga, Zn, and In, and the molecular sieve component comprises ≥99 wt. % of ZSM-5-type zeolite impregnated with the dehydrogenation metal component and/or ion exchanged with the dehydrogenation metal component. For example, the second catalyst can comprise Ga-impregnated and/or In-impregnated H-ZSM-5, Ga-exchanged and/or In-exchanged H-ZSM-5, H-gallosilicate of ZSM-5 type structure and H-galloaluminosilicate of ZSM-5 type structure. Optionally, the second catalyst includes (i) tetrahedral aluminum and/or gallium, which is present in the zeolite framework or lattice, and/or (ii) octahedral gallium or indium, which is not present in the zeolite framework but present in the zeolite channels in close vicinity to the zeolitic protonic acid sites. The tetrahedral or framework Al and/or Ga is believed to contribute to acid function of the catalyst and octahedral or non-framework Ga and/or In is believed to contribute to the dehydrogenation function of the second catalyst. In a particular aspect, the second catalyst comprises H-galloaluminosilicate of ZSM-5 type structure having framework (tetrahedral) Si/Al and Si/Ga atomic ratios of about 10:1 to 100:1 and 15:1 to 150:1, respectively, and non-framework (octahedral) Ga of 0 wt. % to 1 wt. %, e.g., 0 wt. % to 0.5 wt. % or 0.5 wt. % to 1 wt. %.

The second catalyst can be subjected to one or more treatments, e.g., a selectivation treatment to increase selectivity for producing desired aromatic hydrocarbon compounds such as paraxylene. For example, the second catalyst's molecular sieve component can comprise at least one selectivated molecular sieve. The selectivation can be carried out before introduction of the catalyst into the reactor and/or in-situ in the reactor, e.g., by contacting the second catalyst with a selectivating agent, such as at least one organosilicon in a liquid carrier and subsequently calcining the catalyst at a temperature of 350 to 550° C. This selectivation procedure can be repeated two or more times and alters the diffusion characteristics of the catalyst such that the formation of para-xylene over other xylene isomers is favored. Such a selectivation process is described in detail in U.S. Pat. Nos. 5,633,417 and 5,675,047, which are incorporated by reference herein in their entirety.

Typically, the second catalyst has a surface area in the range of from 100 m$^2$/g to 600 m$^2$/g, e.g., in the range of from 200 m$^2$/g to 500 m$^2$/g. When the catalyst comprises aluminosilicate which includes phosphorous, the phosphorous:aluminum atomic ratio is typically in the range of from 0.01 to 0.5. For example, the catalyst can contain ≥10 wt. % of phosphorous-modified alumina, such as ≥15 wt. %, or in the range of from 10 wt. % to 20 wt. %.

Third Catalyst

The third catalyst comprises ≥10 wt. % of the molecular sieve component, and optionally further comprises dehydrogenation and matrix components. When used, the dehydrogenation and matrix components can be the same as those described in connection with the second catalyst. When the third catalyst's molecular sieve component comprises less than 100 wt. % of the catalyst, ≥90 wt. % of the remainder of the catalyst can comprise the specified matrix and/or specified dehydrogenation components, such as ≥99 wt. % of the remainder. In certain aspects, the third catalyst is substantially free of dehydrogenation metal, where substantially free in this context means ≤0.001 wt. % based on the weight of the catalyst.

Unlike the second catalyst, the third catalyst typically has little if any aromatization activity. When present, the relative amount of aromatics in the third product can be determined by measuring the third product's refractive index as disclosed in U.S. Pat. No. 4,021,501, which is incorporated by reference herein in its entirety. Those skilled in the art will appreciate that aromatic activity can be lessened or eliminated by utilizing molecular sieve of controlled acidity. For example, the third catalyst's molecular sieve component typically comprises ≥50 wt. % of at least one molecular sieve having an α≤250, such as ≥90 wt. %, or ≥95 wt. %. The particular value of α typically depends on the type of molecular sieve included in the third catalyst's molecular sieve component. For example, when the molecular sieve component comprises ≥90 wt. % ZSM-5, α is typically in the range of from about 0.1 to 120, such as 0.1 to 100. In other aspects, α is in the range of from 100 to 250, e.g., in the range of 160 to 200. Alternatively or in addition to zeolites previously specified for the third catalyst, the third catalyst's molecular sieve component can comprise one or more of Chabazite, Zeolite Beta, ZSM-4, ZSM-18, ZSM-38 and/or ZSM-57.

Optionally, the third catalyst's molecular sieve component typically has a silica:alumina molar ratio ≥12, e.g., ≥30. The silica:alumina molar ratio is meant to represent the Si:Al atomic ratio in the rigid anionic framework of the crystalline aluminosilicate. In other words, aluminum in (i) any matrix or binder or (ii) in cationic or other form within the crystalline aluminosilicate's channels is excluded from the silica:alumina molar ratio.

The third catalyst's molecular sieve component is typically one that provides constrained access to and egress from the molecular sieve's intra-crystalline free space. Those skilled in the art will appreciate that this can be accomplished by utilizing molecular sieve having a pore dimension ≥5 Å, and pore openings (analogous to windows) of a size such as would be provided by a ten-membered ring of oxygen atoms. Typically, the third catalyst's molecular sieve component comprises ≥50 wt. % of one or more molecular sieves having and an α in the specified range and a Constraint Index in the range of from 1 to 12, e.g., ≥75 wt. %, such as ≥90 wt. %, or ≥95 wt. %. Constraint Index is determined in accordance with the method disclosed in U.S. Pat. No. 4,016,218, and α is determined in accordance with the method disclosed in U.S. Pat. No. 3,960,978, these patents being incorporated herein in their entirety.

Typically, the third catalyst has a surface area in the range of from 100 m$^2$/g to 600 m$^2$/g, e.g., in the range of from 200 m$^2$/g to 500 m$^2$/g. Suitable third catalysts are described in U.S. Pat. Nos. 3,960,978; 4,021,502; 4,150,062; 4,211,640; 4,227,992; and 4,456,781; each of which is incorporated by reference herein in its entirety.

Certain aspects which utilize the second catalyst for dehydrocyclization and which utilize the third catalyst for oligomerization will now be described in more detail. The invention is not limited to these aspects, and this description is not meant to foreclose other catalytic reactions within the broader scope of the invention.

Dehydrocyclization

Referring again to FIG. 1, reaction zone 190 can be operated to produce a second product comprising aromatics and molecular hydrogen. The aromatics and molecular hydrogen are produced at least in part from the corresponding olefinic hydrocarbon of the heated raffinate. The dehydrocyclization is carried out in the presence of at least the second catalyst, which is typically located in at least one bed within reaction zone 190. Conventional fixed, moving, and/or fluidized beds can be used in reaction zone 190, but the invention is not limited thereto.

In reaction zone 190, at least a portion of the heated raffinate is exposed to a catalytically effective amount of the specified second catalyst under catalytic dehydrocyclization conditions that are effective for converting at least a portion of the heated raffinate's corresponding olefinic hydrocarbon, e.g., one or more of ethylene, propylene, and butylenes, to aromatic hydrocarbon and additional molecular hydrogen. The catalytic dehydrocyclization conditions can include exposing the heated raffinate to a temperature in the range of from 400° C. to 650° C., a pressure in the range of from 100 kPa to 2200 kPa. Typically, the catalytic dehydrocyclization conditions further include a space velocity (WHSV) ≥0.1 hr$^{-1}$. More typically, the catalytic dehydrocyclization conditions include a temperature in the range of from 500° C. to 625° C., a pressure in the range of from 30 psia (207 kPa) to 80 psia (522 kPa). Space velocity (WHSV) can be in the range of from 0.1 hr$^{-1}$ to 20 hr$^{-1}$. Typically, the space velocity (WHSV) of $C_{2+}$ hydrocarbon (the "$C_{2+}$ WHSV") in the specified raffinate with respect to the second catalyst is in the range of from 0.1 hr$^{-1}$ to 20 hr$^{-1}$, e.g. 0.2 hr$^{-1}$ to 5 hr$^{-1}$, or 0.3 hr$^{-1}$ to 1 hr$^{-1}$. The $C_{2+}$ WHSV is the hourly rate of the $C_{2+}$ hydrocarbon (in grams per hour) exposed to the second catalyst per gram of the second catalyst. The reaction is typically endothermic. Generally, the average temperature across reaction zone 190 is ≤600° C., more typically in the range of from 20° C. to 200° C., e.g., in the range of from 50° C. to 150° C. Typically, the heated raffinate is not exposed to a temperature ≥630° C. at the inlet to reaction zone 190.

A second product 200 comprising aromatic hydrocarbon and additional molecular hydrogen is conducted away from reaction zone 190. The molecular hydrogen of the second product is "additional" in the sense that it is in addition to those produced in stage 1. If desired, at least a portion of the second product's aromatic hydrocarbon can be separated in one or more separators 210, and conducted away via conduit 220, e.g., for storage and/or further processing. The separated aromatic hydrocarbon can be used e.g., as blend components for transportation fuels, as feed for petrochemical processes for producing one or more of styrene, phenol, nylon, polyurethanes, and xylenes such as paraxylene.

Light hydrocarbon, can be present in the second product. The light hydrocarbon can include, e.g., unreacted feed components, such as unreacted first and/or second hydrocarbon. The second product's light hydrocarbon can also include one or more of (i) $C_{4-}$ hydrocarbon produced in reaction zone 110 (e.g., when separator 140 is not used or operates with less than 100% separation efficiency), (ii) $C_{4-}$ hydrocarbon produced in reaction zone 190, and (iii) any unconverted $C_{4-}$ olefinic hydrocarbon of the heated raffinate. The second product's light hydrocarbon can be recovered, e.g., via conduit 230. At least a portion of the recovered paraffinic hydrocarbon can be utilized for operating one or more of (i) fired heaters for transferring heat to reaction zones 110 and/or 190, (ii) electric power generation, e.g., when electric heating is used to provide at least a portion of the heat needed for sustaining the endothermic reactions of zones 110 and/or 190, and (iii) recycle to line 100 for use as a feed component. Unreacted $C_{4-}$ olefinic hydrocarbon can be recycled to line 180, for example. Molecular hydrogen can be recovered, and optionally combined with molecular hydrogen separated from separator 140. Since the reaction of reaction zone 250 is typically exothermic, heat can be transferred from reaction zone 250 to zones 110 and/or 190 for increased energy efficiency.

Operating reaction zone 190 under the specified conditions with the specified second catalyst generally results in converting ≥5 wt. % of that portion of the corresponding olefinic hydrocarbon of the heated raffinate that is introduced into zone 190, e.g., ≥10 wt. %, such as ≥20 wt. %. In certain aspects, the second product comprises ≥1 wt. % of aromatic hydrocarbon, based on the weight of the second product, e.g., ≥10 wt. %, such as ≥25 wt. %, or ≥50 wt. %, or ≥75 wt. %, or ≥90 wt. %. More particularly, reaction zone 190 typically exhibits an aromatic hydrocarbon yield from the raffinate's corresponding olefinic hydrocarbon ≥20%, e.g., ≥40%, such as in the range of 35% to 70%. While not wishing to be bound by any theory or model, it is believed that the increased feed conversion, the increased selectivity for aromatic hydrocarbon, and the decrease in selectivity for catalyst coke over conventional processes result at least in part from carrying out part of the dehydrogenation in a first stage (to produce olefinic hydrocarbon) and then carrying out the remainder of the dehydrogenation and substantially all of the cyclization in a second stage.

Reaction zone 190 can have one or more stages containing at least one bed of the specified second catalyst (a dehydrocyclization catalyst). The dehydrocyclization catalyst may be in particulate form, with the dehydrocyclization reaction taking place as the raffinate traverses the catalyst bed. The dehydrocyclization catalyst bed may be one or more of a fixed, moving or fluidized catalyst bed. It has been found that it is beneficial for the dehydrocyclization catalyst to have a residence time of ≤90 seconds in the dehydrocyclization reaction zone under dehydrocyclization conditions. It has been discovered that doing so dramatically increases the conversion of $C_{2+}$ hydrocarbon without a significant decrease in the selectivity for aromatic hydrocarbon, and without excessive selectivity for light hydrocarbon compounds such as methane. More particularly, it has been found that it is beneficial for the dehydrocyclization catalyst to have a residence time in reaction zone 190 under dehydrocyclization conditions of ≤60 seconds, e.g., ≤30 seconds, such as ≤10 seconds, or ≤1 second, or ≤0.1 second or in the range of from 0.001 second to 60 seconds. Especially when the second catalyst is present in a moving bed and/or fluidized bed, it is beneficial for it to have a residence time in the dehydrocyclization reaction zone that is in the range of from 0.01 second to 10 seconds, e.g. 0.1 second to 10 seconds, such as 0.1 second to 1 second. After the specified residence time, the dehydrocyclization catalyst is typically at least partially regenerated and then returned dehydrocyclization service. The regeneration can be carried out in reaction zone 190. Alternatively or in addition, the dehydrocyclization catalyst can be removed from the reaction zone after the specified residence time, as least partially regenerated outside of the reaction zone, and then returned to the reaction zone for continued dehydrocyclization after the regeneration.

Oligomerization

In certain aspects, the second stage is operated to produce a third product which includes the oligomer, the oligomer being produced at least in part from the corresponding olefinic hydrocarbon present in the heated raffinate. The oligomerization is carried out in the presence of the third catalyst, which is located in reaction zone 250.

The third product is conducted away from reaction zone 250 via conduit 260. The molecular hydrogen of the second product is "additional" in the sense that it is in addition to those produced in stage 1. If desired, at least a portion of the third product's oligomer can be separated in one or more separators 270, and conducted away via conduit 280, e.g., for storage and/or further processing. The separated oligomer can be used e.g., as a blend component for transportation fuels.

Light hydrocarbon, can be present in the third product. The light hydrocarbon can include, e.g., unreacted feed components, such as unreacted first and/or second hydrocarbon. The third product's light hydrocarbon can also include one or more of (i) $C_4$-hydrocarbon produced in reaction zone 110 (e.g., when separator 140 is not used or operates with less than 100% separation efficiency), (ii) $C_{4-}$ hydrocarbon produced in reaction zone 250, and (iii) any unconverted $C_{4-}$ olefinic hydrocarbon of the heated raffinate. The third product's light hydrocarbon can be recovered, e.g., via conduit 290. At least a portion of the recovered paraffinic hydrocarbon can be utilized for operating one or more of (i) fired heaters for transferring heat to reaction zones 110 and/or 190, (ii) electric power generation, e.g., when electric heating is used to provide at least a portion of the heat needed for sustaining the endothermic reactions of zones 110 and/or 190, and (iii) recycle to line 100 for use as a feed component. Unreacted $C_{4-}$ olefinic hydrocarbon can be recycled to line 180, for example. Depending on the selected catalyst and process conditions, the third product can comprise additional aromatics and additional molecular hydrogen. These can be separated and conducted away from the third product in separator 270 or in an additional separator (not shown).

The catalytic oligomerization conditions generally include a temperature in the range of from 290° C. to 450° C., a hydrocarbon pressure in the range of from 100 kPa to 2000 kPa, and a space velocity (WHSV) in the range of from 0.5 hr$^{-1}$ to 20 hr$^{-1}$. Suitable process conditions are disclosed in U.S. Pat. Nos. 4,211,640 and 4,456,781, for example.

Operating reaction zone 250 under the specified conditions with the specified third catalyst generally results in converting ≥5 wt. % of that portion of the corresponding olefinic hydrocarbon of the heated raffinate that is intruded into zone 250, e.g., ≥10 wt. %, such as ≥20 wt. %. In certain aspects, the third product comprises ≥1 wt. % of the specified, based on the weight of the second product, e.g., ≥10 wt. %, such as ≥25 wt. %, or ≥50 wt. %, or ≥75 wt. %, or ≥90 wt. %. More particularly, reaction zone 250 typically exhibits a total yield of the specified oligomer from the raffinate's corresponding olefinic hydrocarbon ≥50%, e.g., ≥60%, such as in the range of 55% to 75%. While not wishing to be bound by any theory or model, it is believed that the increased conversion and decrease in selectivity for catalyst coke over conventional processes result at least in part from carrying out the dehydrogenation and oligomerization in separate stages. When the feed's first and second hydrocarbon are derived from natural gas, ≥10 Wt. % of the oligomer is typically $C_{5+}$ oligomer, e.g., ≥20 wt. %.

All patents, test procedures, and other documents cited herein, including priority documents, are fully incorporated by reference to the extent such disclosure is not inconsistent and for all jurisdictions in which such incorporation is permitted.

While the illustrative forms disclosed herein have been described with particularity, it will be understood that various other modifications will be apparent to and can be readily made by those skilled in the art without departing from the spirit and scope of the disclosure. Accordingly, it is not intended that the scope of the claims appended hereto be limited to the examples and descriptions set forth herein but rather that the claims be construed as encompassing all the features of patentable novelty which reside herein, including all features which would be treated as equivalents thereof by those skilled in the art to which this disclosure pertains.

When numerical lower limits and numerical upper limits are listed herein, ranges from any lower limit to any upper limit are contemplated, and are expressly within the scope of the invention. The term "comprising" is synonymous with the term "including". Likewise whenever a composition, an element or a group of components is preceded with the transitional phrase "comprising", it is understood that we also contemplate the same composition or group of components with transitional phrases "consisting essentially of", "consisting of", "selected from the group of consisting of", or "is" preceding the recitation of the composition, component, or components, and vice versa.

The invention claimed is:

1. A process for producing aromatics, comprising:
   (a) providing a feed which comprises ≥1 wt. % of a first hydrocarbon and further comprises a second hydrocarbon, wherein (i) the first hydrocarbon comprises $C_{n+}$ paraffinic hydrocarbon, (ii) the second hydrocarbon comprises $C_{m-}$ hydrocarbon, (iii) n is a positive integer ≥2 and m is a positive integer ≤n−1, and (iv) the feed has a first hydrocarbon:second hydrocarbon molar ratio in the range of from 0.001 to 100;
   (b) providing a first multi-component catalyst, the first catalyst having dehydrogenation functionality and comprising (i) ≥10 wt. % of at least one inorganic oxide component having a surface area ≥10 m²/g and a pore volume ≥0.1 ml/g, (ii) ≥0.01 wt. % of at least one catalytically active carbonaceous component, and (iii) ≥0.05 wt. % of at least one element selected from Groups 5-11 of the Periodic Table;
   (c) providing a second multi-component catalyst, the second catalyst having dehydrocyclization functionality and comprising ≥10 wt. % of a molecular sieve component and ≥0.005 wt. % of a dehydrogenation component comprising at least one element selected from Groups 3 to 13 of the Periodic Table;
   (d) reacting the feed in the presence of the first catalyst under catalytic dehydrogenation conditions effective for dehydrogenating ≥10 wt. % of the $C_{n+}$ paraffinic hydrocarbon of the feed's first hydrocarbon to produce a first product comprising corresponding olefinic hydrocarbon, $C_{m-}$ hydrocarbon, and molecular hydrogen; and
   (e) reacting ≥10 wt. % of the first product's corresponding olefinic hydrocarbon in the presence of the second catalyst under catalytic dehydrocyclization conditions to produce a second product comprising aromatics and additional molecular hydrogen.

2. The process of claim 1, wherein the first catalyst's inorganic oxide component comprises silica and/or alumina.

3. The process of claim 1, wherein the first catalyst's catalytically active carbonaceous component (i) comprises ≥90 wt. % of carbon and/or carbide, and (ii) has the morphology of one or more of (A) one or more graphene layers, (B) a plurality of nanotubes, and (C) a plurality of nanofibers.

4. The process of claim 1, wherein component (iii) of the first catalyst comprises one or more metals selected from V, Cr, Mn, Fe, Co, Ni, Pt, Pd, Ru, Au, Mo, and Rh.

5. The process of claim 1, wherein the second catalyst comprises ≥20 wt. % of the molecular sieve component and ≥0.1 wt. % of the dehydrogenation component.

6. The process of claim 1, wherein the second catalyst's molecular sieve component comprises one or more of MCM-22, ZSM-5, ZSM-11, ZSM-12, ZSM-22, ZSM-23, ZSM-35, and ZSM-48.

7. The process of claim 1, wherein the second catalyst's dehydrogenation component comprises two or more of Ga, Zn, Cu, Re, Mo, W, La, Fe, Ag, Pt, and Pd.

8. The process of claim 1, wherein n=2 and m=1.

9. The process of claim 1, wherein:
   (i) the feed's first hydrocarbon is a mixture of ethane, propane, and butanes;
   (ii) the feed's second hydrocarbon comprises methane;
   (iii) the feed comprises 10 wt. % to 40 wt. % of the ethane, 20 wt. % to 50 wt. % of the propane, and 20 wt. % to 50 wt. % of the butanes;
   (iv) the feed has a first hydrocarbon:second hydrocarbon molar ratio in the range of from 0.01 to 0.05; and
   (v) the feed comprises ≤1 wt. % of $C_{5+}$ hydrocarbon and ≤1 wt. % of diluent.

10. The process of claim 9, wherein
    (i) the catalytic dehydrogenation conditions include a temperature in the range of from 500° C. to 650° C., a pressure ≥15 psia (103 kPa), and a space velocity (WHSV) ≥0.1 hr⁻¹, and
    (ii) the catalytic dehydrocyclization conditions include a temperature in the range of from 500° C. to 625° C., a pressure in the range of from 30 psia (207 kPa) to 80 psia (522 kPa), and a $C_{2+}$ space velocity (WHSV) in the range of from 0.1 hr⁻¹ to 20 hr⁻¹.

11. A process for producing aromatic hydrocarbon, comprising:
    (a) providing a synthesis hydrocarbon for catalyst synthesis, the synthesis hydrocarbon comprising ≥50 wt. % of at least one $C_{2+}$ paraffinic hydrocarbon compound;
    (b) providing a catalyst precursor comprising at least one element selected from Groups 5-11 of the Periodic Table and at least one inorganic oxide having a surface area ≥10 m²/g and a pore volume ≥0.1 ml/g;
    (c) exposing the catalyst precursor to a flow of the synthesis hydrocarbon at a temperature in the range of from 500° C. to 750° C., a pressure ≥15 psia (103 kPa), and a space velocity (WHSV) ≥0.1 hr⁻¹, to produce a first multi-component catalyst having dehydrogenation functionality, the first catalyst comprising (i) ≥10 wt. % of at least one inorganic oxide component having a surface area ≥10 m²/g and a pore volume ≥0.1 ml/g, (ii) ≥0.01 wt. % of at least one catalytically active carbonaceous component, and (iii) ≥0.05 wt. % of at least one element selected from Groups 5-11 of the Periodic Table;
    (d) providing a feed which comprises ≥1 wt. % of a first hydrocarbon and further comprises a second hydrocarbon, wherein the (i) the first hydrocarbon comprises $C_{n+}$ paraffinic hydrocarbon, (ii) the second hydrocarbon comprises $C_{m-}$ hydrocarbon, (iii) n is a positive integer ≥2 and m is a positive integer ≤n−1, and (iv) the feed has a first hydrocarbon:second hydrocarbon molar ratio in the range of from 0.001 to 100;
    (e) reacting the feed in the presence of the first catalyst under catalytic dehydrogenation conditions effective for dehydrogenating ≥10 wt. % of the of the $C_{n+}$ paraffinic hydrocarbon of the feed's first hydrocarbon to produce a first product comprising corresponding olefinic hydrocarbon, $C_{m-}$ hydrocarbon, and molecular hydrogen;
    (f) providing a second multi-component catalyst, the second catalyst having dehydrocyclization functionality and comprising ≥10 wt. % of a molecular sieve component and ≥0.1 wt. % of a dehydrogenation component comprising at least one element selected from Groups 3 to 13 of the Periodic Table; and
    (g) reacting ≥10 wt. % of the first product's corresponding olefinic hydrocarbon in the presence of the second catalyst under catalytic dehydrocyclization conditions to produce a second product comprising aromatics and additional molecular hydrogen.

* * * * *